US00PP12048P2

(12) United States Plant Patent

Nagatomi et al.

(10) Patent No.: US PP12,048 P2

(45) Date of Patent: Aug. 14, 2001

(54) *CYTISUS SCOPARIUS L* PLANT NAMED 'MEI KING'

(75) Inventors: Shigeki Nagatomi, Ibaraki; Hiroyuki Anzai; Kazuko Katsumata, both of Kanagawa, all of (JP)

(73) Assignees: National Institute of Agrobiological Resources, Ministry of Agriculture, Forestry and Fisheries, Tsukuba; Meiji Seika Kaisha, Ltd., Tokyo, both of (JP)

( * ) Notice: Subject to any disclaimer, the term of this patent is extended or adjusted under 35 U.S.C. 154(b) by 0 days.

(21) Appl. No.: 09/274,959

(22) Filed: Mar. 23, 1999

(30) Foreign Application Priority Data

Mar. 31, 1998 (JP) ..... 10-10758

(51) Int. Cl.[7] ..... A01H 5/00

(52) U.S. Cl. ..... Plt./226

(58) Field of Search ..... Plt./226

(56) References Cited

U.S. PATENT DOCUMENTS

P.P. 10,811 * 3/1999 Berry ..... Plt./226

OTHER PUBLICATIONS

Dirr, M.A. Manual of Woody Landscape Plants, p. 1145. Stipes Publishing, Ilinois, 1998.*

* cited by examiner

*Primary Examiner*—Bruce R. Campell
*Assistant Examiner*—Melissa L. Kimball
(74) *Attorney, Agent, or Firm*—Armstrong, Westerman, Hattori, McLeland & Naughton, LLP

(57) ABSTRACT

A new variety of *C. scoparius L.* named 'MEI KING' is a dwarf shrub suitable for use a potted plant, garden shrub or ground cover.

2 Drawing Sheets

The present invention relates to a new and distinct horticultural variety of *Cytisus scoparius L.*

BACKGROUND OF THE INVENTION

*C. scoparius L.* is a woody shrub of the pulse family originally from Middle Europe and the coast of the Mediterranean Sea. Horticultural varieties of *C. scoparius L.* having flowers in various colors such as yellow, white, red, cream and mixed colors etc. have been bred. The majority of such varieties are erect and low to slightly tall in height, although there are some which are dwarf such as creeping varieties. Because of the drawback of the required trimming and selection, *C. scoparius L.* is rarely used for ornamental planting.

However, *C. scoparius L.* presents the advantage of vigorous growth even in unfertile wasteland, so if a dwarf variety having a wide variety of flower colors could be bred, its use as a ground cover, ornamental shrub, etc. will be possible, with a wide variety of applications to be expected.

The present inventors have developed a new dwarf variety of *C. scoparius L.* by a combination of mutagenesis by rapid irradiation and tissue culture technique, as described below:

1. In July 1990, pods of the original species 'CRIMSON KING', formed after 3 weeks of flowering, were externally sterilized in The Institute of Radiation Breeding, National Institute of Agrobiological Resources, Ministry of Agriculture, Forestry and Fisheries, Oomiya-cho, Naka-gun, Ibaraki Pref., Japan. Young embryos removed from these pods were irradiated with gamma rays of Co 60 and 100 Gy for 72 hours.

2. The young embryos thus irradiated were cultivated in an MS agar medium containing plant hormones (i.e., naphthalene acetic acid and benzyl adenine) at 25° C. for a day length of 16 hours, whereby re-differentiated plants were obtained via multi-blastema and shoots after callus induction.

3. In March 1991, the young plants sufficiently rooted in sterile medium were transferred to potting media in pots in a greenhouse, then acclimated therein, and transferred to a field.

4. Selection of a dwarf plant from the respective plants was conducted on the basis of plant height, plant width, internode length, etc. as indicators.

5. Evaluation of the practical characteristics of the resulting selected strain was carried out in the Institute of Radiation Breeding, National Institute of Agrobiological Resources, Ministry of Agriculture, Forestry and Fisheries. In reproducing selected plants, branches were selected from the Institute of Radiation Breeding in June; cuttings each approximately 10 cm long were planted in sterilized river sand or vermiculite; and rooted plants were cultivated in a mist room. After April 1993, the evaluation was conducted in Ashigara Farm of Meiji Seika Kaisha Ltd. in Kayama, Odawara City, Kanagawa Pref., Japan, and the present variety, which was judged to be a promising dwarf plant based on the examination results obtained up to May 1997, was finally selected.

The present 'MEI KING' variety has a cup-shaped spreading form and extreme dwarfism with a mature height of 35 cm. Leaf attachment is sparse with many flowers borne from the base of branches, the flowers being deep red and larger than those of the original variety.

BOTANICAL DESCRIPTION

Figure 1:
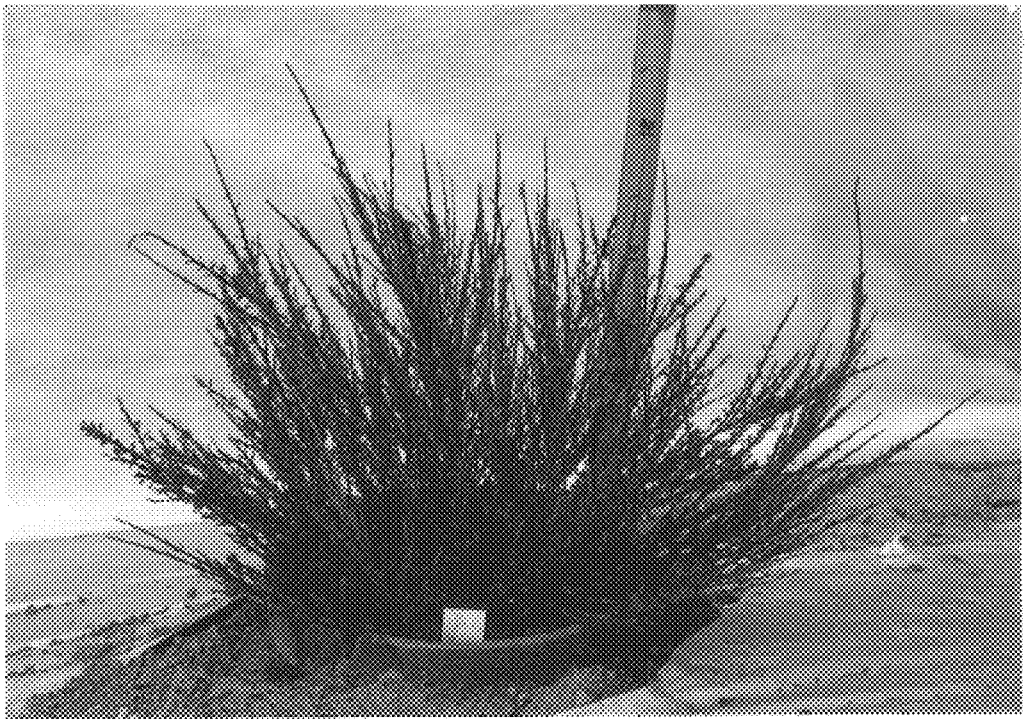
FIG. 1 shows the variety 'MEI KING'.
Figure 2:
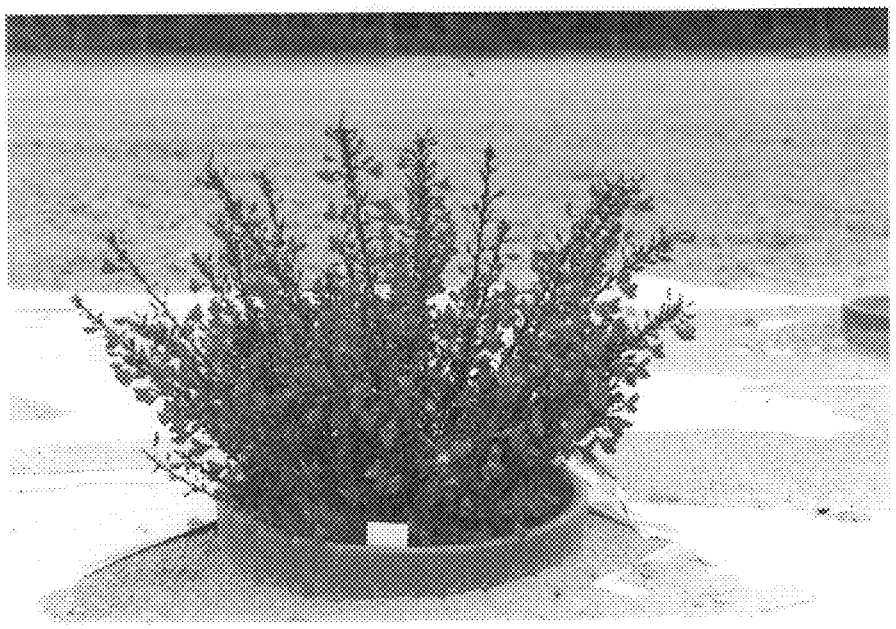
FIG. 2 shows the variety 'MEI KING' at flowering time.
Figure 3:
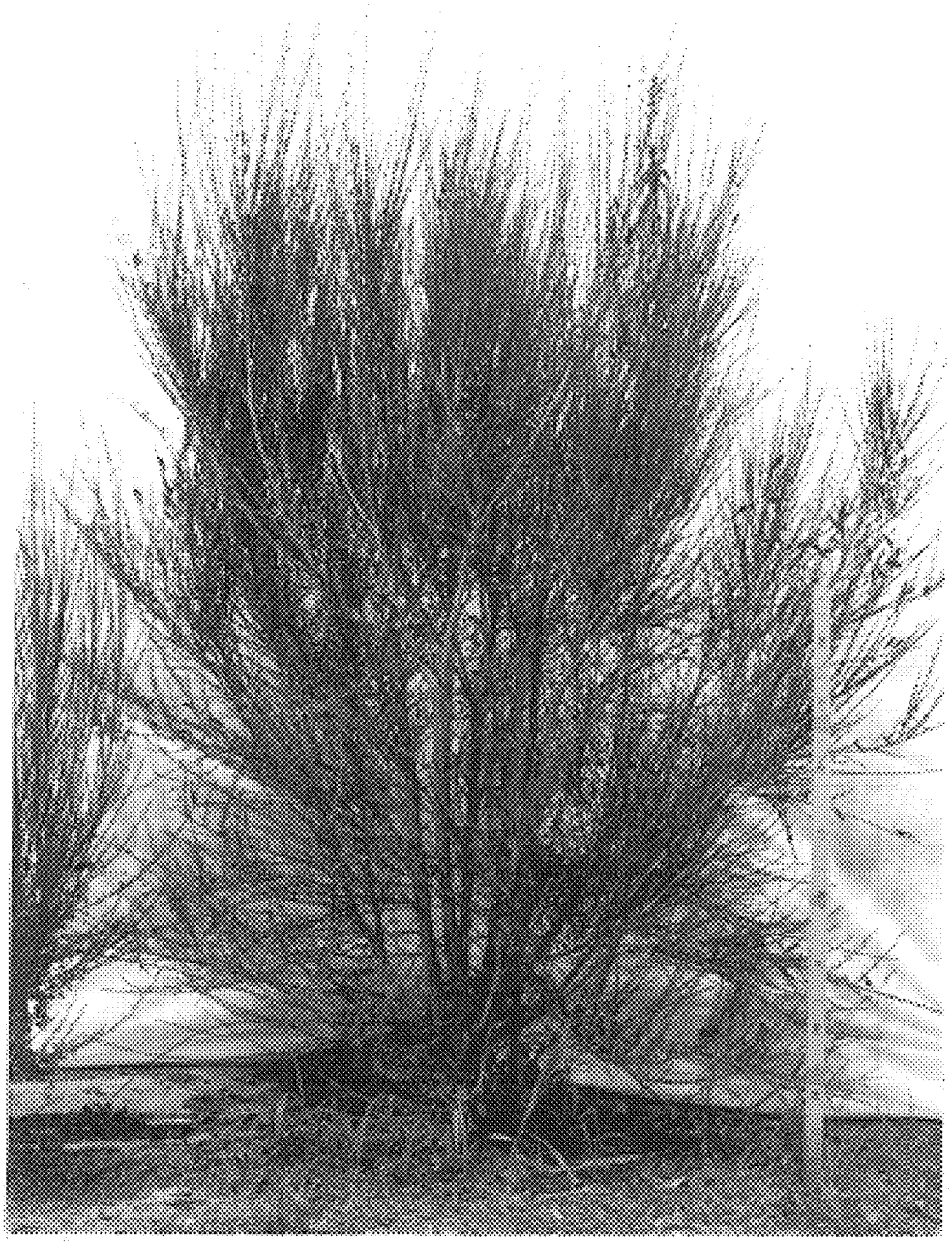
FIG. 3 shows the original variety 'CRIMSON KING'.

The original variety 'CRIMSON KING' is erect in form, while 'MEI KING' is prostrate, with spreading and cup-shaped form. The original variety is tall, with a plant height of about 160 cm, while 'MEI KING' is very dwarf, having a mature plant height of about 35 cm. The internode length is 0.9 cm, which is shorter than in the original variety. The leaf length is 11 cm, which is shorter than that of the original variety, and the petiole length is also shorter. The leaves are sparse as compared to the original variety. The standard petal is 21.5 mm in length and 19.1 mm in width, and the wing petal is 20 mm in length and 9.2 mm in width, and these are similar to those of the original variety.

The shape of a floral bud is long elliptic and its color is deep red. When it blooms, the entire surfaces of both the adaxial and abaxial sides of a standard petal uniformly turn to a deep red color. The adaxial face of a wing petal is deep red while the abaxial face of the wing petal is light yellow. The standard petal and the wing petal of the present variety are comparatively larger than those of the original variety. The overall size of the flower is also larger, and the color of the flower deeper, in comparison to the original variety. Filaments are yellow and curvedly projected from petals with yellow anthers at the tips thereof. Pistils are hidden behind petals and invisible from the outside. The flower emits a fragrance characteristic of leguminosae. The total bloom period lasts approximately one month, and the prime of bloom is 7 to 10 days, which is a most valuable term for a decorative plant. Sexual fertility is poor, and few flowers become fertilized. Vegetative propagation by cuttings is required for reproduction.

The distinctive characteristics of 'MEI KING' have been examined in plants cultured at Ashigara Farm in the period 1993–1997 as described above, according to the examination standards based on the Japanese Seeds and Seedlings Law. The characteristics of 'MEI KING' are set forth below, as compared to the variety 'CRIMSON KING'.

| Characteristic | 'MEI KING' | 'CRIMSON KING' |
|---|---|---|
| Plant vigor | weak to medium | medium to strong |
| Plant form | flat circle to flat | elliptic |
| Plan height | low (35 cm in 5-year mature plant) | tall to very tall (160 cm) |
| Direction of branching | spreading to greatly spreading | erect to spreading |
| Internode length | short (0.9 cm) | medium (1.1 cm) |
| Leaf composition | mixture of single (one leaflet) and compound (two or three leaflets) in varying ratio | mixture of single (one leaflet) and compound (two or three leaflets) in varying ratio |
| Leaf shape | long elliptic | long elliptic |
| Color of leaf | green | green–deep green |
| Shape of leaf tip | sharp to obtuse | sharp to obtuse |
| Shape of leaf edge | smooth | smooth |
| Warp of leaf | convexly warped to flat | convexly warped to flat |
| Length of leaf | short to medium (11.0 mm) | medium to long (12.3 mm) |
| Width of leaf | medium (3.0 mm) | medium (3.5 mm) |
| Length of petiole | short (5–10 mm) | medium |

-continued

| Characteristic | 'MEI KING' | 'CRIMSON KING' |
|---|---|---|
| Leaf | sparse | medium |
| Color of new shoots | light red | light red |
| Pubescence of new shoots | little | little |
| Shape of flower bud | long elliptic | long elliptic |
| Size of flower bud | medium | medium |
| Size of flower | medium to large | medium |
| Color of standard petal (surface) | red<br>JHS: 0415<br>RHS: 53C | red<br>JHS: 0415<br>RHS: 53C |
| Color of standard petal (back) | red<br>JHS: 0415<br>RHS: 53C | white to yellow<br>JHS: 2202<br>RHS: 18C<br>19C<br>20D<br>158A<br>162D<br>164D |
| Color of wing petal (surface) | red<br>JHS: 0415<br>RHS: 53C | red<br>JHS: 0415<br>RHS: 53C |
| Color of wing petal (back) | white to yellow<br>JHS: 2202<br>RHS: 18C<br>19C<br>20D<br>158A<br>162D<br>164D | white to yellow<br>JHS: 2202<br>RHS: 18C<br>19C<br>20D<br>158A<br>162A<br>164D |
| Length of standard petal | short to medium (21.5 mm) | short (20.1 mm) |
| Width of standard petal | medium (19.1 mm) | medium (17.5 mm) |
| Length of wing petal | short (20.0 mm) | short (19.6 mm) |
| Width of wing petal | narrow (9.2 mm) | narrow (9.1 mm) |
| No. of stamen | medium | medium |
| Branch sprouting time | seasonal, late sprouting begins around March | late |
| Flowering time (70–80%) | average, begins mid-April to mid-May | average |
| Leaf falling time | average, begins around October and completed mid-winter | average |
| Disease resistance | no susceptibility to any serious disease, but susceptible to inchworm | |
| Culture | can survive in poor soil if well drained, but root damage if poorly drained. | |

The 'MEI KING' cultivar has not been observed under all possible environmental conditions to date. Accordingly, it is possible that the phenotype may vary somewhat with variations in the environment, such as temperature, light intensity, and day length.

We claim:

1. A new and distinct variety of *Cytisus scoparius L.* plant named 'MEI KING' substantially as shown and described herein.

* * * * *